United States Patent [19]

Hickmann

[11] Patent Number: 5,124,488
[45] Date of Patent: Jun. 23, 1992

[54] POLYTETRAHYDROFURAN ETHERS

[75] Inventor: Eckhard Hickmann, Dannstadt-Schauerheim, Fed. Rep. of Germany

[73] Assignee: BASF Aktiengesellschaft, Ludwigshafen, Fed. Rep. of Germany

[21] Appl. No.: 520,032

[22] Filed: May 7, 1990

[30] Foreign Application Priority Data

May 30, 1989 [DE] Fed. Rep. of Germany ....... 3917457

[51] Int. Cl.$^5$ .............................................. C07C 43/15
[52] U.S. Cl. .................................... 568/616; 568/622
[58] Field of Search ................ 549/472; 568/616, 622

[56] References Cited

U.S. PATENT DOCUMENTS 4,548,752 10/1985 Pentz ..................................... 549/502
4,595,537 6/1986 Ochiai et al. ......................... 568/616

FOREIGN PATENT DOCUMENTS 0400436 12/1990 European Pat. Off. ............ 568/616

OTHER PUBLICATIONS

*Chemical Abstracts* vol. 98, No. 216044p, 1983, Ryuzo et al., "A Kinetic Study of the Radical Polymerization of Polytetrahydrofuran Macromer".

Chemical Abstract, vol. 105, #1922560, Liedloff et al., 1986, "Use of thermoplastic polyether-polyamide to prepare flexible materials with low-temperature toughness".

Chemical Abstract, vol. 98 #216,044, Asami et al., 1983, "A kinetic study of the radical polymerization of polytetrahydrofuran macromer".

Houben-Weyl, "Methoden der organischen Chemie", vol. 6/3, (1965) pp. 23-26.

J. Am. Chem. Soc. 83 (1961), p. 1701.
J. Am. Chem. Soc. 83 (1961), p. 1773.

*Primary Examiner*—C. Warren Ivy
*Assistant Examiner*—Raymond Covington
*Attorney, Agent, or Firm*—John H. Shurtleff

[57] ABSTRACT

Polytetrahydrofuran ethers of the formula $$R^1\text{-}[O-(CH_2)_4]_n\text{-}O\text{-}R^2 \qquad I$$

where n is a number from 3 to 70, and $R^1$ and $R^2$ are hydrocarbon radicals containing 3 to 5 carbon atoms and a double bond, but where $R^2$ may alternatively be hydrogen.

6 Claims, No Drawings

POLYTETRAHYDROFURAN ETHERS

The present invention relates to novel polytetrahydrofuran ethers of general formula $$R^1\text{---}[O\text{---}(CH_2)_4]_nO\text{---}R^2 \qquad \text{I}$$

where n is a number from 3 to 70, and $R^1$ and $R^2$ are aliphatic hydrocarbon radicals containing 3 to 5 carbon atoms and a double bond, but where $R^2$ may alternatively be hydrogen.

The novel polytetrahydrofuran ethers of the formula I are useful building blocks for polymers.

The hydrocarbon radicals $R^1$ and $R^2$ present in the polytetrahydrofuran ethers are, for example, radicals of the formulae $$CH_2\text{=}CH\text{---}CH_2\text{---}, \quad CH_3\text{---}CH\text{=}CH\text{---},$$

$$CH_3\text{---}C(CH_3)\text{=}CH\text{---}, \quad CH_2\text{=}C(CH_3)\text{---}CH_2\text{---} \text{ and}$$

$$CH_3\text{---}CH\text{=}CH\text{---}CH_2\text{---}.$$

Novel polytetrahydrofuran ethers have, for example, the formula $$\underset{\underset{H_2C\text{=}C\text{---}CH_2\text{---}[O\text{---}(CH_2)_4]_n\text{---}O\text{---}R^4}{|}}{R^3} \qquad \text{II}$$

where $R^3$ is hydrogen or methyl, $R^4$ is hydrogen or the radical of the formula $\text{---}CH_2\text{---}C(R^3)\text{=}CH_2$, and n is a number from 3 to 70, or the formula $$\underset{\underset{H_3C\text{---}C\text{=}CH\text{---}[O\text{---}(CH_2)_4]_n\text{---}O\text{---}R^5}{|}}{R^3} \qquad \text{III}$$

where $R^3$ is hydrogen or methyl, $R^5$ is hydrogen or the radical of the formula $\text{---}CH\text{=}C(R^3)\text{---}CH_2$, and n is a number from 3 to 70.

Polytetrahydrofurans of the general formula $$H\text{---}[O(CH_2)_4]_n\text{---}OH \qquad \text{IV}$$

(called PTHF below) are prepared, for example, by cationic polymerization of tetrahydrofuran (called THF below). In the structural formula IV, the degree of polymerization n indicates the number of THF-derived oxybutane-1,4-diyl units per molecule and is usually n=3 (corresponding to a mean molecular weight of $\overline{MW}$=234) to about 70 (corresponding to an $\overline{MW}$ of about 5,000). The degree of polymerization n or the mean molecular weight $\overline{MW}$ corresponding to this value, through which the PTHF mixtures obtainable on polymerization of THF are characterized, can be determined, for example, by osmometric or titrimetric analyses. The following PTHF mixtures, for example, are particularly important in industry: PTHF 250 ($\overline{MW}$=about 250, $\bar{n}$=about 3), PTHF 650 ($\overline{MW}$=about 650, $\bar{n}$=about 9), PTHF 1000 ($\overline{MW}$=about 1000, $\bar{n}$=about 14), PTHF 2000 ($\overline{MW}$=about 2000, $\bar{n}$=about 27), PTHF 2900 ($\overline{MW}$=about 2900, $\bar{n}$=about 40) and PTHF 4500 ($\overline{MW}$=about 4500, $\bar{n}$=about 62).

Each of these PTHF mixtures contains a broad range of PTHF homologs, whose number is from about 10 to 20 in the low molecular weight range and increases to more than 30 in the high molecular weight range.

PTHF is used as an α,ω-diol for the preparation of polymers. In this case, its valuable properties distinguish PTHF as a building block for elastomeric and thermoplastic polymers (P. Dreyfuss "Handbook of Elastomers, New Developments and Technology", 1988, p. 695).

As an α,ω-diol, however, the reactivity of PTHF is limited to the typical reactions of primary alcohols. There has therefore been no lack of attempts to influence the reactivity of PTHF by modifying the end groups in order thereby to broaden its possible uses. Thus, for example, the reaction of PTHF with diisocyanates in the molar ratio 1:2 gives PTHF-diurethanes containing free, terminal isocyanate groups, and transesterification of (meth)acrylates using PTHF gives PTHF bis(meth)acrylates. In reactions of this type with mixtures of PTHF homologs, mixtures of homologous PTHF derivatives which again differ structurally only through the different number of recurring oxybutane-1,4-diyl units in the polyether chain are again obtained.

The present invention relates to the novel polytetrahydrofuran ethers of the general formula I. They are prepared, for example, by conventional methods (see Houben-Weyl, "Methoden der organischen Chemie", Volume 6/3, pp. 23-36) by reacting a) polytetrahydrofurans of the general formula $$H\text{---}[O\text{---}(CH_2)_4]_n\text{---}OH \qquad \text{IV}$$

where n is as defined above, with compounds of the general formula $$R^1\text{-}X \qquad \text{V}$$

where $R^1$ is as defined above, X is halogen or a radical of the formula $\text{---}SO_2\text{---}R^6$, and $R^6$ is alkyl having 1 to 6 carbon atoms, or by reacting b) polytetrahydrofuran derivatives of the formula $$X\text{---}(CH_2)_4\text{---}[O(CH_2)_4\text{---}O]_{n-2}(CH_2)_4\text{---}X \qquad \text{VI}$$

where X and n are as defined above, with alcohols of the formula $$R^1\text{-}OH \qquad \text{VII}$$

where $R^1$ is as defined above. In these reactions, the reactants are used, for example, in a molar ratio of from 2:1 to 1:2. The reaction is carried out, for example, at up to 100° C., preferably 0° to 80° C., and in the presence of basic substances. Suitable basic substances are preferably tertiary amines, for example trialkylamines, such as tributylamine, triethylamine, N,N-dimethylaniline or heterocyclic nitrogen compounds containing a tertiary nitrogen atom, such as pyridine, picoline and quinoline. However, the basic substances employed may alternatively be carbonates, hydroxides or hydrides of the alkali metals or alkaline earth metals, such as potassium carbonate, potassium hydroxide or sodium hydride, or alkoxides, such as potassium tertiary-butoxide.

The basic substances are employed, for example, in stoichiometric amounts, relative to the compound V or VI, but it is also possible to use a superstoichiometric or substoichiometric amount of from 10 to 20%.

The reaction is expediently carried out in a solvent. Suitable solvents are all those which do not react with the reactants under the reaction conditions and in which PTHF or the PTHF derivative is soluble, ie. ethers, such as methyl tert.-butyl ether (MTBE), diethyl ether, dioxane or tetrahydrofuran, carbonyl compounds, such as acetone, methyl ethyl ketone, methyl isobutyl ketone or ethyl acetate, aliphatic hydrocarbons, such as cyclohexane, methylene chloride or dichloroethane, or aromatic hydrocarbons, such as toluene, benzene or xylene. However, it is also possible to carry out the reaction in the abovementioned tertiary amines The reaction mixtures are worked up, for example, in a simple manner by adding water, separating off the organic phase, washing the latter with water in order to remove salts formed and, where appropriate, the solvent, and removing the residual solvent by distillation.

The novel polytetrahydrofuran ethers of the formula III can also be obtained from the corresponding alkyl ethers of the formula II by a conventional base-catalyzed isomerization (J. Amer. Chem. Soc., 1961, 83, 1701-1704 and 1773). The isomerization is carried out, for example, at from 130° to 180° C. in the presence of basic substances, such as alkali metal alkoxides, in particular potassium tert.-butoxide and sodium tert.-amylate.

The PTHF derivatives according to the invention are used as comonomers in polyolefins and polyvinyl ethers and as crosslinking agents in hydroxyl-containing polymers, inter alia in dispersions.

$^1$H NMR spectroscopy is particularly suitable for the identification and assay of the PTHF ethers according to the invention.

EXAMPLE 1

Preparation of PTHF 650 bisallyl ether 305 g of allyl chloride are added at 60°-65° C. over the course of 3 hours to a stirred mixture of 520 g of PTHF 650, 2.4 l of toluene, 536 g of KOH powder and 3 g of triethylamine. The reaction mixture is allowed to react for a further 4.5 hours and then washed by stirring with 600 ml of water, and the organic phase is washed with 200 ml of water. The low-boiling components are removed on a rotary evaporator, and the residue is dried in an oil-pump vacuum at 80° C. to give 579 g of PTHF 650 bisallyl ether ($\bar{n}$=about 9.0).

The NMR spectrum of the product exhibits the multiplet at $\delta$=3.9–4.0 (2×2 H), 5.1–5.3 (2×2 H) and 5.8–6.0 (2×1 H) which are typical of the allyloxy groups. A mean molecular weight of 748 (calculated: 730) and a bromine number of 42.8 (measured: 42) can be derived from the intensity ratios of all the NMR bands. No alcohol groups can be detected analytically.

EXAMPLE 2

Preparation of PTHF 1000 bisallyl ether 22. 8 g of allyl chloride are added at 23°-24° C. over the course of 1 hour to a stirred mixture of 100 g of PTHF 1000, 300 ml of toluene, 64 g of KOH powder and 1.0 g of tetrabutylammonium bromide, and the mixture is stirred for a further 12 hours. The work-up described under Example 1 gives 104.9 g of PTHF 1000 bisallyl ether ($\bar{n}$=13.9).

The NMR spectrum of the product exhibits the multiplet (see Example 1) which is typical of the allyl-oxy groups. A mean molecular weight of 1097 (calculated: 1080) and a bromine number of 29.2 (measured: 30) can be derived from the intensity ratios of all the NMR bands. No alcohol groups can be detected analytically.

EXAMPLES 3-9

Examples 3-11, listed in Table 1, were carried out in the same manner as Examples 1 and 2:

TABLE 1

| Example | PTHF (MW) n | Amount (g) | Reagent formula V | Amount (g) | Base Formula | Amount (g) | Solvent Type | Amount (ml) | React. temp. (°C.) | React. duration (h) |
|---|---|---|---|---|---|---|---|---|---|---|
| 3 | 250 | 200 | ⟋⟍Cl | 305 | KOH N(C₂H₅)₃ | 536 3 | toluene | 2400 | 45-62 | 24 |
| 4 | 250 | 25 | ⟋⟍Cl | 16.8 | KOH 18-crown-(6) | 25.6 1.05 | THF | 100 | 20-24 | 12 |
| 5 | 650 | 130 | ⟋⟍Cl | 38 | NaH | 10.1 | MTBE | 300 | 30-54 | 12 |
| 6 | 1000 | 100 | ⟋⟍Cl | 19.1 | KOH N(C₂H₅)₃ | 48 0.3 | toluene | 300 | 22-26 | 48 |
| 7 | 1000 | 100 | ⟋⟍Cl | 22.8 | KOH Aliquat 336 | 64 1.2 | toluene | 300 | 22-27 | 12 |
| 8 | 2000 | 1000 | ⟋⟍Cl | 191.4 | KOH N(C₂H₅)₃ | 335.7 1.88 | toluene | 1500 | 45-50 | 18 |
| 9 | 250 | 100 | ⟋⟍Cl (methallyl) | 181 | KOH N(C₂H₅)₃ | 268 1.5 | toluene | 1000 | 60 | 3 |
| 10 | 650 | 260 | ⟋⟍Cl (methallyl) | 181 | KOH N(C₂H₅)₃ | 268 1.5 | toluene | 1200 | 60 | 8 |
| 11 | 1000 | 100 | ⟋⟍Cl (methallyl) | 27.2 | KOH (n-C₄H₉)₄NBr | 48 1.5 | toluene | 500 | 45-50 | 18 |

| | | Product | | | |
|---|---|---|---|---|---|
| | | MW | | Bromine number | |
| Example | Amount (g) | Cal. | Acc. to NMR $\bar{n}$ | Acc. to NMR | Measured |

TABLE 1-continued

| | | | | | | |
|---|---|---|---|---|---|---|
| 3 | 257 | 330 | 325 | 3.1 | 98.5 | 98 |
| 4 | 28.5 | 330 | 331 | 3.2 | 96.7 | 97 |
| 5 | 138.5 | 730 | 743 | 8.9 | 43.1 | 44 |
| 6 | 104 | 1080 | 1081 | 13.6 | 29.6 | 30 |
| 7 | 107 | 1080 | 1092 | 13.8 | 29.3 | 30 |
| 8 | 1014 | 2080 | 2053 | 27.1 | 15.6 | 16 |
| 9 | 139 | 358 | 367 | 3.3 | 87.2 | 88 |
| 10 | 285 | 758 | 749 | 8.6 | 42.7 | 42 |
| 11 | 107 | 1108 | 1115 | 13.7 | 28.7 | 29 |

EXAMPLE 12

Preparation of PTHF 250 bispropenyl ether

A mixture of 60.8 g of PTHF 250 diallyl ether (n=3.2) and 3.0 g of potassium tert.-butoxide is heated at 150° C. for 3 hours under nitrogen. After cooling, 100 ml of water and 100 ml of methyl tert.-butyl ether are added to the reaction mixture, which is then neutralized using carbon dioxide, and the organic phase is separated off and washed with 100 ml of water. The solvent is removed and the residue dried in an oil-pump vacuum at 80° C. to give 58.5 g of PTHF 250 bispropenyl ether ($\bar{n}$=3.3).

The NMR spectrum of the product exhibits the multiplet at δ=1.6 (2×3 H), 4.3–4.45 (2×1 H) and 5.9–6.0 (2×1 H) which is typical of the propyleneoxy groups. A mean molecular weight of 333 (calculated: 330) and an iodine number of 152 (measured: 150) can be derived from the intensity ratios of all the NMR bands.

EXAMPLES 13 to 17

Examples 13 to 17, listed in Table 2, were carried out in the same manner as Example 10.

2. A polytetrahydrofuran ether of the formula $$H_2C=C(R^3)-CH_2+O-(CH_2)_4+_nO-R^4 \quad II$$

where $R^3$ is hydrogen or methyl, $R^4$ is hydrogen or the radical of the formula $-CH_2-C(R^3)=CH_2$, and n is a number from 3 to 70.

3. A polytetrahydrofuran ether of the formula $$H_3C-C(R^3)=CH+O-(CH_2)_4+_nO-R^5 \quad III$$

where $R^3$ is hydrogen or methyl, $R^5$ is hydrogen or the radical of the formula $-CH=C(R^3)-CH_3$, and n is a number from 3 to 70.

4. A polytetrahydrofuran ether as claimed in claim 1, wherein $R^1$ and $R^2$ are each identical and selected from the group consisting of $CH_2=CH-CH_2-$, $CH_3-CH=CH-$, $CH_3-C(CH_3)=CH-$, $CH_2=C(CH_3)-CH_2-$ and $CH_3-CH=CH-CH_2-$.

TABLE 2

| Example | PTHF ether of the formula II employed | Amount (g) | KO^tBu(2) (g) | React. temp. (°C.) | React. duration (h) | PTHF ether of the formula III obtained | $\bar{n}$ | Amount (g) | $\overline{MW}$ Calc.(1) | Acc. to NMR | Iodine number Acc. to NMR | Measured |
|---|---|---|---|---|---|---|---|---|---|---|---|---|
| 13 | PTHF 650 diallyl ether | 115.0 | 3.0 | 150 | 6 | PTHF 650 dipropenyl ether | 8.9 | 111.4 | 743 | 741 | 68.5 | 68 |
| 14 | PTHF 2000 diallyl ether | 480 | 6.1 | 145–155 | 5 | PTHF 2000 dipropenyl ether | 27.3 | 472 | 2053 | 2068 | 24.5 | 25 |
| 15 | PTHF 250 di(2-methyl-allyl) ether | 74.0 | 3.2 | 150 | 6 | PTHF 250 di(2-methyl-propenyl) ether | 3.1 | 72.1 | 367 | 352 | 144.2 | 146 |
| 16 | PTHF 650 di(2-methyl-allyl) ether | 130.5 | 2.7 | 150 | 3.5 | PTHF 650 di(2-methyl-propenyl) ether | 8.8 | 125.8 | 749 | 761 | 66.7 | 65 |
| 17 | PTHF 1000 di(2-methyl-allyl) ether | 55.8 | 3.2 | 150–155 | 6 | PTHF 1000 di(2-methyl-propenyl) ether | 13.4 | 54.0 | 115 | 1092 | 46.5 | 47 |

(1)Mean molecular weight of the PTHF (meth)allyl ether employed
(2)Potassium tert.-butoxide

We claim:

1. A polytetrahydrofuran ether of the formula $$R^1+O-(CH_2)_4]_nO-R^2 \quad I$$

where n is a number from 3 to 70, and $R^1$ and $R^2$ are aliphatic hydrocarbon radicals containing 3 to 5 carbon atoms and a durable bond, but where $R^2$ may alternatively be hydrogen.

5. A polytetrahydrofuran ether as claimed in claim 4 wherein $R^1$ and $R^2$ are each $CH_2=CH-CH_2-$.

6. A polytetrahydrofuran ether as claimed in claim 4 wherein $R^1$ and $R^2$ are each $$CH_2=C(CH_3)-CH_2-.$$

* * * * *